(12) United States Patent
Michels et al.

(10) Patent No.: US 9,821,305 B2
(45) Date of Patent: Nov. 21, 2017

(54) METHOD FOR HEATING A VOLUME OF LIQUID IN A HEATED PIPETTING NEEDLE

(71) Applicant: Siemens Healthcare Diagnostics Products GmbH, Marburg (DE)

(72) Inventors: Thorsten Michels, Gross-Gerau (DE); Ayhan Selvi, Bingen (DE); Alexander Wiedekind-Klein, Steinbach (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 395 days.

(21) Appl. No.: 13/753,858

(22) Filed: Jan. 30, 2013

(65) Prior Publication Data

US 2013/0195718 A1   Aug. 1, 2013

(30) Foreign Application Priority Data

Jan. 31, 2012 (EP) .................................. 12153208

(51) Int. Cl.
| | |
|---|---|
| *B01L 3/02* | (2006.01) |
| *F16L 53/00* | (2006.01) |
| *B01L 7/00* | (2006.01) |
| *G01N 35/00* | (2006.01) |
| *G01N 35/10* | (2006.01) |

(52) U.S. Cl.
CPC ............... *B01L 3/021* (2013.01); *B01L 3/02* (2013.01); *B01L 7/00* (2013.01); *F16L 53/00* (2013.01); *B01L 2200/147* (2013.01); *B01L 2300/0838* (2013.01); *B01L 2300/18* (2013.01); *B01L 2300/1888* (2013.01); *G01N 35/10* (2013.01); *G01N 2035/00425* (2013.01); *Y10T 137/0318* (2015.04)

(58) Field of Classification Search
CPC ........ B01L 3/02; B01L 3/0217; B01L 3/0237; B01L 2200/14; B01L 2200/143; B01L 2300/1888
USPC ......................... 436/180; 422/501, 509–524; 73/864.01–864.25
See application file for complete search history.

(56) References Cited

U.S. PATENT DOCUMENTS

| | | | |
|---|---|---|---|
| 5,287,758 A | 2/1994 | Geiss et al. | |
| 6,576,477 B1 | 6/2003 | Tokiwa et al. | |
| 7,438,861 B2 | 10/2008 | Hochstrasser et al. | ....... 422/547 |
| 7,850,921 B2 | 12/2010 | Iguchi et al. | .............. 73/863.11 |
| 8,418,929 B2 | 4/2013 | Tajima | ......................... 236/1 R |
| 2001/0017060 A1 | 8/2001 | Offen et al. | |
| 2004/0259268 A1* | 12/2004 | Jacobs et al. | ................. 436/180 |

(Continued)

FOREIGN PATENT DOCUMENTS

| | | | |
|---|---|---|---|
| AU | 654995 B2 | 12/1994 | ................ B01L 3/02 |
| DE | 4423267 A1 | 1/1996 | |

(Continued)

OTHER PUBLICATIONS

European Search Report of European Patent Application No. 12153208.9 dated Jul. 20, 2012.

(Continued)

*Primary Examiner* — Jan Ludlow
(74) *Attorney, Agent, or Firm* — Slayden Grubert Beard PLLC

(57) ABSTRACT

The invention relates to a pipetting device for automatic analysis instruments and a method for heating a volume of liquid in a heated pipetting needle.

5 Claims, 2 Drawing Sheets

(56) References Cited

U.S. PATENT DOCUMENTS

2008/0044311 A1    2/2008  Iguchi et al.
2010/0163111 A1*   7/2010  Tajima .............................. 137/3

FOREIGN PATENT DOCUMENTS

| EP | 0496962 A2    | 8/1992  |              |
|----|---------------|---------|--------------|
| EP | 1134024 A2    | 9/2001  |              |
| EP | 1859870 A1    | 11/2007 |              |
| EP | 2145949 A1    | 1/2010  |              |
| JP | 0663424 A     | 3/1994  | ............ B01L 3/02 |
| JP | 2001174465 A  | 6/2001  | ............ G01N 35/00 |
| JP | 2007326098 A  | 12/2007 | ............ B01J 4/02 |
| JP | 2008070355 A  | 3/2008  | ............ B67D 99/00 |
| JP | 2011099681 A  | 5/2011  | ............ G01N 35/00 |
| WO | 2008/126827 A1| 10/2008 | ............ C12M 1/00 |
| WO | 2009035981 A1 | 3/2009  |              |

OTHER PUBLICATIONS

Japanese Office Action, Application No. 2013014609, 4 pages, Nov. 8, 2016.
Japanese Office Action, Application No. 2013014609, 4 pages, dated Nov. 8, 2016.

* cited by examiner

METHOD FOR HEATING A VOLUME OF LIQUID IN A HEATED PIPETTING NEEDLE

PRIORITY STATEMENT

The present application hereby claims priority under 35 U.S.C. §119 of European Patent Application Number EP12153208.9, filed Jan. 31, 2012, the entire contents of which are hereby incorporated herein by reference.

FIELD OF INVENTION

The invention lies in the field of automatic or semiautomatic analysis instruments and relates to a pipetting device and a method for heating a volume of liquid in a heated pipetting needle.

BACKGROUND OF INVENTION

Pipetting devices are used in automatic or semiautomatic analysis instruments for clinical diagnostics, biotechnology, environmental analysis or substance analysis. Analytic methods are carried out in such analysis instruments by virtue of liquid samples and/or reagents being mixed to form a reaction mixture and the reaction being measured quantitatively, for example by photometric means. Automatically controlled pipetting devices, which usually work like a suction pipette, are used to transfer precisely metered volumes of liquid samples or reagents from storage containers to reaction containers.

Many instruments are able to pick up a multiplicity of samples and to store a multiplicity of reagents. For reasons of storage, the reagent supplies in particular are cooled in the reagent station to a temperature below room temperature. However, in order to carry out an analytical method, particularly if it is based on enzymatic reactions, it is necessary for there to be a specific temperature in the reaction mixture. It is for this reason that use has been made for a long time of warmed pipetting needles, which make it possible to adjust the temperature of the liquid to be transferred to the desired value prior to dispensing it to the reaction container. By way of example, heated pipetting devices are described in EP-A2-1134024, EP-A2-0496962 or US 2008/0044311 A1.

Modern analysis instruments are able to carry out many different tests. This means that the pipetting devices must be able to pipette different volumes of various cooled reagents and, in doing so, be able to heat these to the desired reaction temperature or to a temperature in the vicinity of the desired reaction temperature.

In known analysis instruments, use is made of pipetting devices which should constantly have the same intended temperature. In instruments for analyzing blood, plasma or serum samples, the target temperature for the reagents to be pipetted is conventionally 37° C. The temperature of the pipetting needle is measured with the aid of thermosensors. The heating device is only activated if the temperature of the pipetting needle drops below the set intended value temperature.

In practice, it is a problem to ensure that different volumes of liquid are equally heated to the same target temperature, e.g. to 37° C. Under certain circumstances, relatively large volumes are not heated sufficiently, smaller volumes are possibly overheated, or vice versa. Volumes that are so small that they only remain in the region of the suction tip of the pipetting needle are possibly not heated sufficiently either, because the region of the suction tip often is not heated at all or because there is a temperature gradient along the pipetting needle and the suction tip simply has a lower temperature than the remaining part of the pipetting needle.

In US 2008/0044311 A1, this problem is solved by virtue of the fact that the temperature in the pipetting device is matched to the volume of liquid to be transferred. The larger the volume of liquid to be transferred is, the more strongly the pipetting needle is heated. The pipetting needle is also heated more strongly in the case of particularly small volumes. A disadvantage of this method is that this requires a complicated control of the heating device and that the heating device must be embodied such that it is able to heat the pipetting needle differently from one pipetting step to the next. This particularly is a problem if a large volume of liquid which needs to be heated less strongly is initially pipetted and this is directly followed by a smaller volume of liquid which needs to be heated more strongly. In this case, there is the risk that the smaller volume is not heated enough from the still less strongly heated pipetting needle.

SUMMARY OF INVENTION

The object of the present invention was therefore to provide means and methods which render it possible to use a conventional pipetting device which constantly has the same intended temperature to heat different volumes of liquid equally to the desired target temperature.

This object is achieved by virtue of the fact that the pipetting needle initially draws in the desired volume of liquid and subsequently additionally draws in a volume of air, as a result of which the volume of liquid reaches deeper into the pipetting needle. The volume of air is selected such that the volume of liquid reaches the region of the heated pipetting needle in which the temperature sensor is mounted and completely passes through this region.

The invention therefore relates to a method for heating a volume of liquid in a heated pipetting needle with a closed-loop controllable heating device and a region in which a temperature sensor is mounted, wherein the method comprises the following steps:

drawing in the desired volume of liquid and then
drawing in a volume of air,
wherein the volume of air is selected such that the volume of liquid reaches the region of the heated pipetting needle in which the temperature sensor is mounted and completely passes through this region.

BRIEF DESCRIPTION OF THE DRAWINGS

A more complete appreciation of the present invention and many of the attendant advantages thereof will be readily understood by reference to the following detailed description when taken in conjunction with the accompanying drawings, in which.

DETAILED DESCRIPTION OF INVENTION

Figure 1:
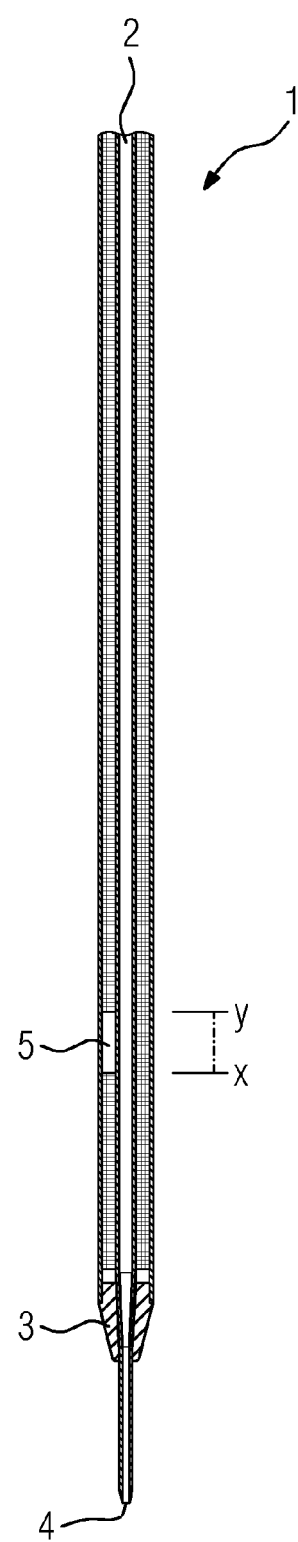
FIG. 1 shows a heatable pipetting needle (1), which consists of a cylindrical hollow needle made of stainless steel.

It was found that drawing in an additional volume of air is more efficient at obtaining uniform heating of various volumes of liquid than, for example, an incubation between drawing in and dispensing, i.e. the volume of liquid to be pipetted remaining in the pipetting needle for a relatively long period of time.

The temperature sensor which measures the temperature of the pipetting needle is preferably in a region of the pipetting needle which, where possible, determines any change in the temperature during drawing in, but at the same time also ensures correct setting of the intended temperature over the whole length of the needle. This region is typically situated in the front third of the needle.

The term "region of the heated pipetting needle in which the temperature sensor is mounted" should be understood such that this is the section along the longitudinal axis of the pipetting needle whose length corresponds to the dimensions of the temperature sensor.

A further subject of the present invention relates to a device for pipetting a volume of liquid, wherein the device comprises the following components:
  a heatable pipetting needle with a closed-loop controllable heating device and a region in which a temperature sensor is mounted;
  means for setting a constant intended temperature of the pipetting needle;
  means for setting a desired volume of liquid to be drawn in;
  means for setting a volume of air to be drawn in, wherein the volume of air to be drawn in is selected dependent on the volume of liquid to be drawn in such that the previously drawn-in volume of liquid reaches the region of the pipetting needle in which the temperature sensor is mounted and completely passes through this region.

Here, "means for setting a constant intended temperature of the pipetting needle" should be understood to mean a closed-loop controller, which receives the information relating to the actual value temperature of the pipetting needle from the thermosensor, compares the actual value temperature to the set intended value temperature and, only if the actual value temperature drops below the set intended value temperature, activates the heating device.

"Means for setting a desired volume of liquid to be drawn in" should be understood to mean a data-processing unit, which contains or receives information relating to the desired volume of liquid to be drawn in and which controls the pipetting devices as per this information such that the latter draws in the desired volume. The information relating to a volume of liquid to be drawn in can for example be stored on a storage medium as part of an information package which defines a specific test method.

"Means for setting a volume of air to be drawn in" should be understood to mean a data-processing unit, which contains or receives information relating to the desired volume of air to be drawn in and which controls the pipetting device as per this information such that the latter draws in the desired volume. The information relating to a volume of air to be drawn in can for example be stored on a storage medium as part of an information package which defines a specific test method. Alternatively, the information relating to a volume of air to be drawn in can be stored on a storage medium as part of an information package which assigns every volume of liquid to be drawn in a volume of air to be drawn in. In any case, the volume of air to be drawn in is selected such that the previously drawn-in volume of liquid reaches the region of the pipetting needle in which the temperature sensor is mounted and completely passes through this region.

A further subject of the present invention relates to an analysis instrument for automatically analyzing samples, preferably bodily fluid samples, comprising a device according to the invention for pipetting a volume of liquid.

An analysis instrument according to the invention preferably further comprises a device for measuring optical properties of a reaction mixture, for example a photometer, and an instrument control. The instrument control comprises a data-processing appliance (computer) and a control unit, as well as optionally a screen and a keyboard.

The control unit controls the work processes of the measuring device, the pipetting device and other technical components of the instrument. Furthermore, the control apparatus stores, processes and analyzes information such as e.g. the measurement data established by the measuring device. The control unit inter alia comprises a hard disk drive on which various computer programs are installed, and a processor (CPU) which executes the installed computer programs. An analysis instrument according to the invention comprises a control unit in which a program is installed on the hard disk drive, which controls the method according to the invention for heating a volume of liquid in a heated pipetting needle by virtue of controlling the desired volume of liquid to be drawn in and then the volume of air to be drawn in.

FIG. 1

FIG. 1 shows a heatable pipetting needle (1), which consists of a cylindrical hollow needle made of stainless steel. At one end, the hollow needle has an opening (2), which can be connected to a drawing-in system, e.g. to a cylinder and a piston which can move therein. At the other end, the hollow needle has a conically shaped tip section (3) with an opening (4). A heating wire is wound around the hollow needle with the exception of the conically shaped tip section (3). The hollow needle has a thermosensor (5). The region of the heated pipetting needle, in which the temperature sensor has been mounted, extends from x to y and corresponds to the extent of the temperature sensor along the longitudinal axis of the pipetting needle.

FIG. 2

A graph illustrating the measured dispensing temperatures of various sample volumes of a cooled sample liquid after being transferred through a heated pipetting needle as per the exemplary embodiment. Curve 1: drawn-in volume of air: 5 µL, incubation time: 0 s; curve 2: drawn-in volume of air: 5 µL, incubation time: 500 ms; curve 3: drawn-in volume of air: 15 µL, incubation time: 0 s; curve 4 (method according to the invention): drawn-in volume of air: 25 µL, incubation time: 0 s.

Example

A heatable pipetting needle, as shown in FIG. 1, was set to an intended temperature of 41° C. and various volumes (9-185 µL) of cold water at 6° C. were aspirated as sample from a cooled storage vessel and dispensed into a storage vessel. The temperature of the water during the dispensing from the pipetting needle was measured with the aid of a transducer, which was mounted horizontally over the capture vessel. Various pipetting procedures were tested, during which the duration time of the sample (incubation time) and/or the quantity of the volume of air which was drawn in after the liquid sample was drawn in were varied. The various parameters are listed in table 1.

TABLE 1

|  | Test 1 | Test 2 | Test 3 | Test 4 |
| --- | --- | --- | --- | --- |
| Drawn-in volume of air | 5 μL | 5 μL | 15 μL | 25 μL |
| Incubation time | 0 | 500 ms | 0 | 0 |

Figure 2:
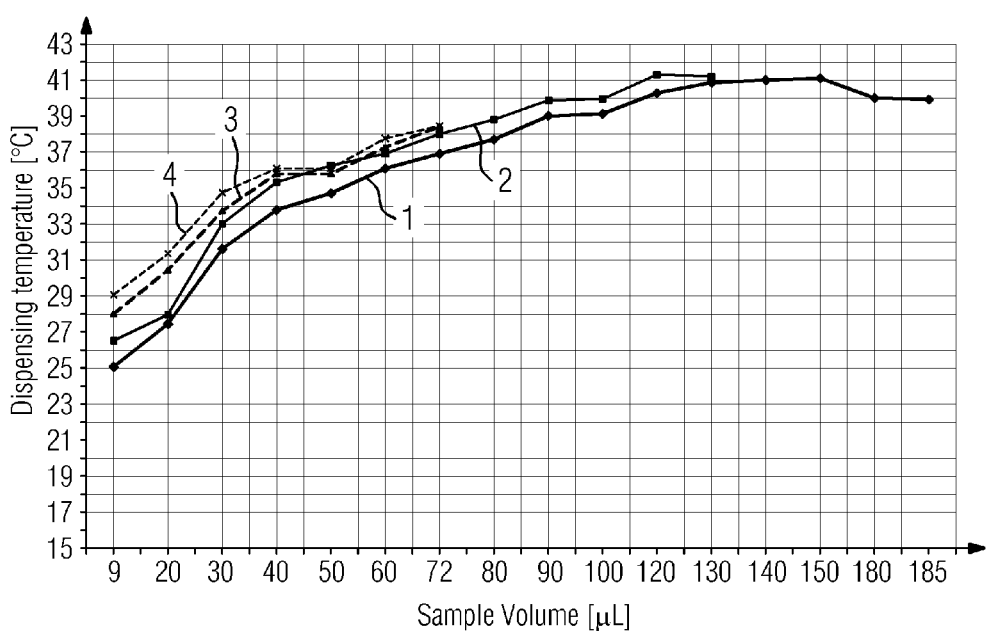
FIG. 2 shows a graph illustrating the measured dispensing temperatures of various sample volumes of a cooled sample liquid after being transferred through a heated pipetting needle as per the exemplary embodiment.

The measured dispensing temperatures of the various pipetted sample volumes are illustrated by a graph in FIG. 2. The deeper the sample volume is drawn into the hollow needle, the more strongly the sample is heated and the dispensing temperature approaches the intended temperature. If the results of test 2 are compared to the results of tests 3 and 4, it becomes apparent that the additional drawing-in of a sufficiently large volume of air brings about a more efficient heating than an increased duration time (incubation) of the sample volume in the pipetting needle. The best result, particularly in respect of small volumes, is achieved if the additionally drawn-in volume of air is so large that the whole sample volume completely passes through the region in which the thermosensor is mounted. In the utilized pipetting needle, the thermosensor was mounted such that a volume of 16 μL of air was required in order to let a volume of liquid completely pass through the thermosensor.

The invention claimed is:

1. A device for pipetting a volume of liquid, wherein the device comprises the following components:
   a) a heatable pipetting needle comprising (i) a cylindrical needle body and a conical needle tip at a downstream end of the cylindrical needle body, (ii) a closed-loop controllable heating device comprising a heating wire wound around the needle along a longitudinal heated section extending substantially the length of the cylindrical needle body, the conical needle tip being free of the heating device, and (iii) a sensor region located longitudinally within the longitudinal heated section such that the longitudinal heated section extends beyond the sensor region both upstream and downstream of the sensor region, the sensor region having a temperature sensor mounted therein;
   b) a closed loop controller for setting a constant intended temperature of the pipetting needle; and
   c) a data-processing unit configured for:
   setting a volume of liquid to be drawn into the pipetting needle; and
   setting a volume of air to be drawn into the pipetting needle after a set volume of liquid is drawn into the pipetting needle, wherein the volume of air is set based on the set volume of liquid such that a previously drawn-in set volume of liquid will extend along at least a portion of the longitudinal heated section for a distance extending both upstream and downstream of the sensor region in which the temperature sensor is mounted.

2. The device according to claim 1, wherein the data-processing unit is configured to set a volume of air to be drawn into the pipetting needle after a set volume of liquid is drawn into the pipetting needle, such that a set volume of liquid will pass completely through the region of the heated pipetting needle having the temperature sensor mounted therein.

3. An analysis instrument for automatically analyzing samples, comprising:
   a device for pipetting a volume of liquid, the device comprising:
   a) a heatable pipetting needle comprising (i) a cylindrical needle body and a conical needle tip at a downstream end of the cylindrical needle body, (ii) a closed-loop controllable heating device comprising a heating wire wound around the needle along a longitudinal heated section extending substantially the length of the cylindrical needle body, the conical needle tip being free of the heating device, and (iii) a sensor region located longitudinally within the longitudinal heated section such that the longitudinal heated section extends beyond the sensor region both upstream and downstream of the sensor region, the sensor region having a temperature sensor mounted therein;
   b) a closed loop controller for setting a constant intended temperature of the pipetting needle;
   c) a data-processing unit configured for:
   setting a volume of liquid to be drawn into the pipetting needle; and
   setting a volume of air to be drawn into the pipetting needle after a set volume of liquid is drawn into the pipetting needle, wherein the volume of air is set based on the set volume of liquid such that a previously drawn-in set volume of liquid will extend along at least a portion of the longitudinal heated section for a distance extending both upstream and downstream of the sensor region in which the temperature sensor is mounted; and
   a reaction container configured to receive the volume of liquid from the heatable pipetting needle, wherein the liquid is reacted with at least one sample or reagent to form a reaction product; and
   an analysis unit configured to analyze the reaction product.

4. The analysis instrument as claimed in claim 3, wherein the data-processing unit for setting a volume of liquid to be drawn in, sets the volume of liquid to be drawn in on the basis of information which defines a specific test method.

5. The analysis instrument as claimed in claim 3, wherein the data-processing unit for setting a volume of air to be drawn in, sets the volume of air to be drawn in on the basis of information which defines a specific test method.

* * * * *